United States Patent
Zwingenberger

[11] Patent Number: 6,048,201
[45] Date of Patent: Apr. 11, 2000

[54] ARRANGEMENT FOR MIXING AND DELIVERING A MULTICOMPONENT MOLDING COMPOUND

[76] Inventor: Arthur Zwingenberger, Rigistr. 36, 6006 Luzern, Switzerland

[21] Appl. No.: 09/173,298

[22] Filed: Oct. 14, 1998

[30] Foreign Application Priority Data

Oct. 15, 1997 [DE] Germany ............... 197 45 614

[51] Int. Cl.$^7$ ................................................. A61C 5/04
[52] U.S. Cl. .............................................. 433/90; 222/137
[58] Field of Search .................. 433/90; 222/105, 222/326, 386

[56] References Cited

U.S. PATENT DOCUMENTS

| | | |
|---|---|---|
| 4,067,479 | 1/1978 | Moline . |
| 4,986,443 | 1/1991 | Saur et al. . |
| 5,033,650 | 7/1991 | Colin et al. ............... 433/90 |
| 5,332,122 | 7/1994 | Herold et al. . |
| 5,401,169 | 3/1995 | Fleisher et al. ............ 433/90 |
| 5,419,460 | 5/1995 | Herold et al. . |
| 5,443,181 | 8/1995 | Popp et al. . |
| 5,501,368 | 3/1996 | Brandhorst et al. . |
| 5,653,360 | 8/1997 | Brandhorst et al. . |
| 5,743,436 | 4/1998 | Wilcox et al. ............ 433/90 |

FOREIGN PATENT DOCUMENTS

| | | |
|---|---|---|
| 0313519A1 | 10/1988 | European Pat. Off. . |
| 0541972 A1 | 10/1992 | European Pat. Off. . |
| 0663348 A1 | 12/1994 | European Pat. Off. . |
| 2537022 A1 | 8/1975 | Germany . |
| 4231421 A1 | 9/1992 | Germany . |
| 4335970 A1 | 10/1993 | Germany . |
| 295185631 U1 | 11/1995 | Germany . |
| 29606463A1 U | 9/1996 | Germany . |

*Primary Examiner*—Todd E. Manahan
*Attorney, Agent, or Firm*—Nims, Howes, Collison, Hansen & Lackert

[57] ABSTRACT

The invention pertains to a device (10) for mixing and delivering a multicomponent molding compound. The device has a receptacle (16) having pistons (58,60) that can be operated by means of a drive unit for emptying at least two film bags (22,24) filled with individual components of the multicomponent molding compound, a static mixer (30) and a headpiece (28), connected to the film bags (22,24). The headpiece has separated flow channels (52) open towards the film bags (22,24) and leading into the static mixer (30). The static mixer (30), the headpiece (28) and the film bags (22, 24) form an integral unit (32) which is disposable, the unit inserted into and removed from the receptacle (16) after its use.

9 Claims, 8 Drawing Sheets

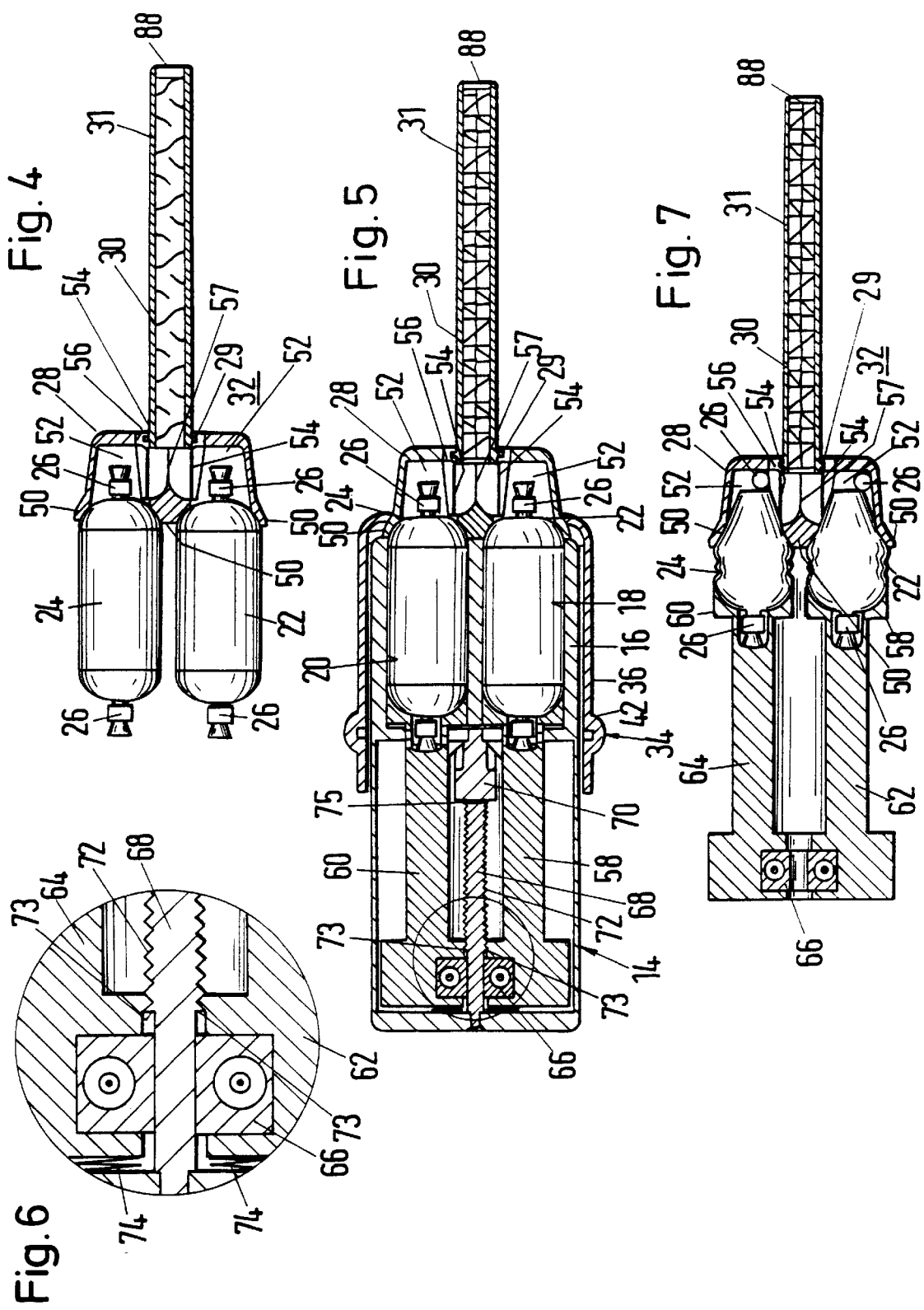

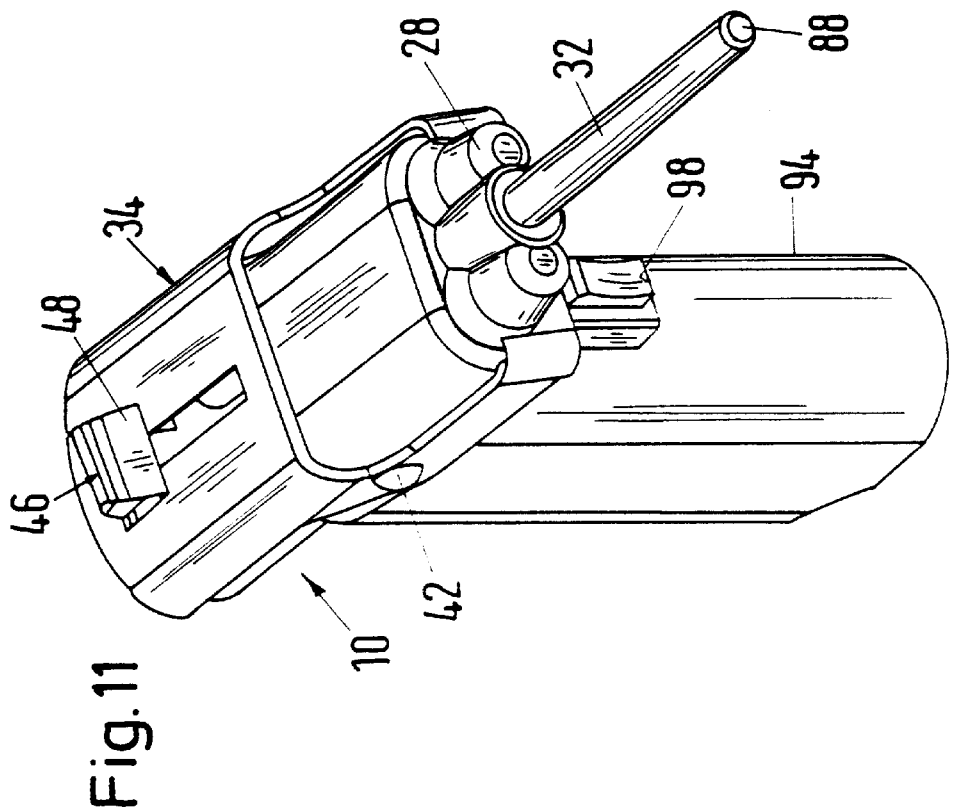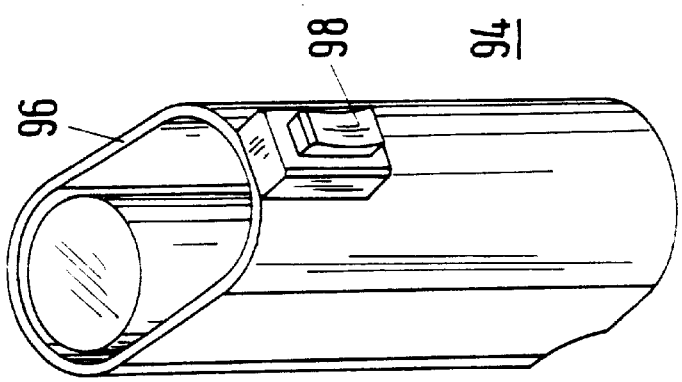

ARRANGEMENT FOR MIXING AND DELIVERING A MULTICOMPONENT MOLDING COMPOUND

TECHNICAL FIELD

The invention pertains to an arrangement for a device for mixing and delivering a multicomponent molding compound.

BACKGROUND

From EP-OS 0 663 348 A1 a device is known for emptying a film tube on the end of which is provided a ring whose edge area exceeds the inside diameter of a cartridge accommodating the film tube. The ring features a conical sealing surface which interacts with a sealing edge formed in the interior of a cap. When put into operation, the cap is pushed with its rear cylindrical end area onto a front end area of the cartridge, wherein the ring is centered and oriented axially and radially with a sealing surface in order to guarantee a proper engagement between sealing edge and sealing surface. The cap is penetrated by a delivery opening. This device is also utilized for the production of multicomponent mixtures.

In EP-OS 0 541 972 A1 a container for a multicomponent compound is disclosed. For each of the components a film tube is provided, each closed off with a clip at each side and each having a ring at one side, which is glued to the film tube. Each of the film tubes is inserted into one of two cylindrical chambers of a double cylinder. At one end face of the double cylinder, a headpiece is provided which is provided with a delivery opening for each of the housing chambers. The two delivery channels are constructed as crimped flow channels situated closely side by side and issuing into a nozzle. A bayonet mount or a screw mount is provided on the headpiece for fastening the nozzle to the headpiece. The nozzle is constructed as a static mixer.

In DE 296 06 463 U1 a device for emptying a tubular bag is disclosed, which features a headpiece in which two bags are arranged. The bags form a constructive unit, in which the bags are glued to the flange of the headpiece. Two separated flow channels lead to a mixing head which is placed onto a nipple.

In DE 43 35 970 A1 a headpiece with film bags as a constructive unit is likewise embodied, wherein a static mixer can be screwed onto the exit connector.

In order to avoid congestion of the headpieces, particularly the flow channels from becoming clogged in the case of curable multicomponent compounds, the halves of the headpiece are respectively marked by color, so that the user always places each component of a molding compound on the same side of the headpiece. In this way, each component is prevented from coming into contact with residues of the other component even inside the delivery openings, thus hardening and clogging the delivery openings and the static mixer.

As experience has shown, such constructions of devices are not only elaborate and expensive in production, but also unsatisfactory in use. As is known, a new mixer must be placed on the headpiece for each mixing process to generate a molding compound, for instance a hardenable impression-molding compound for dentistry purposes, since between two uses, unless they take place one immediately after the other, a hardening of the mixed components in the static mixer takes place.

So far, the static mixer has always had to remain connected to the headpiece in order to avoid a drying out and mixing of the components after use. The static mixers are exchanged only before the next usage. Before its next use, the static mixer, contaminated with blood, bacteria and so on, represents a permanent source of infection. Additionally, the dentist must touch the contaminated static mixer to exchange it, which creates a source of infection for the new patient.

When changing the static mixer, each time there is a movement transverse to the divided opening, whereby components in the opening area become mixed and react, that is, they solidify into a plug that clogs both the inlet to the static mixer and the flow channel of the headpiece. Additionally, the film bags must each be exchanged and one comes into contact with the individual substances via their exit openings. In order to avoid an unintended adhesion here as well, the headpieces must be cleaned which takes an extraordinary amount of time.

The pistons of the device are actuated in part by way of a hand lever. An application with a steady hand is thus not possible.

On the other hand, there is a need in everyday practice, particularly among dentists, for secure operating devices, which considerably ease the production of the aforementioned impression-molding compound for dentistry purposes in the respective volume desired. At the same time, adhesion of individual components to the fingers or to dental technicians'apparatus during exchange is extremely undesirable.

The invention is based on the problem of refining a device for mixing and delivering a multicomponent molding compound such that, while avoiding the aforementioned disadvantages, the operating readiness of the device can be guaranteed by simple means.

This problem is solved by the characteristics of the present invention.

SUMMARY OF THE INVENTION

The invention is based on the recognition that, by forming all components coming into contact with the multicomponent molding compound as an inseparably joined constructive unit, embodied in particular as a disposable item, not only is the danger of undesired contamination by the individual components or a mixing together of the components ruled out, but the risk of contamination in case of dentistry use is also markedly reduced.

According to the invention, the static mixer, the headpiece and the film bag form an inseparably joined constructive unit, which, in particular, can be inserted into and removed from the receptacle of the device as a disposable item.

In this way, it is insured that, in use in dentistry, the static mixer, which could possibly be contaminated with blood, bacteria or the like, is essentially sterile at each use and can be disposed of immediately after usage. The part of the device which enters the patient's mouth, namely, the mixer and possibly the headpiece, is renewed each time.

According to another embodiment of the invention, an entry of the clamping elements detached from the film bag into the static mixer is prevented by inserting a grating, screen or the like between the chamber and the static mixer. In particular, the mixer and the grating, screen or the like are constructed in one piece.

In order both to guarantee a secure connection between the headpiece and the film bags and to prevent an undesired damaging of the film bags by the headpiece, the headpiece has, on its side turned towards the film bags, recipient surfaces arranged symmetrically to the entry opening of the static mixer and adapted to the shape of the filled film bags, to which the film bags are firmly joined, in particular, glued, welded or the like.

According to one embodiment of the invention, at least the end of the film bag turned towards the headpiece is closed off with a clamping means, such as a clip or the like, which detaches from it under increasing internal pressure in the film bag and releases a delivery opening in the film bag. Thus it is achieved that the film bag is securely closed off on the one hand and, on the other, can be easily opened if needed.

According to an alternative embodiment of the invention, the end of the film bag turned towards the headpiece is provided with a material weakening in the film of the film bag which serves as a planned rupture point and opens under increasing internal pressure of the film bag.

The weakening can be produced, for instance, by laser material removal. The weakening must be designed such that, on the one hand, a sufficiently large opening results upon the bursting of the film bag and, on the other hand, no film parts detach from the film tube to impair the exiting of the components.

Additional advantages and characteristics result from the description below of several embodiments of the invention in connection with the drawings.

BRIEF DESCRIPTION OF THE DRAWINGS

FIG. 4 is a sectional view of the constructive unit consisting of static mixer, headpiece and the two film bags;

FIG. 5 is a cross-sectional view through the manual device of FIG. 1;

FIG. 6 is an enlarged partial view from FIG. 5;

FIG. 7 is a sectional view of the pistons, the film bags, the headpiece and static mixer of FIG. 5, where the film bags are partially emptied;

FIG. 11 is a perspective representation of the manual device with an alternative drive unit;

FIG. 12 is a perspective view of the housing of FIG. 11; and

DETAILED DESCRIPTION OF THE INVENTION

Figure 1:
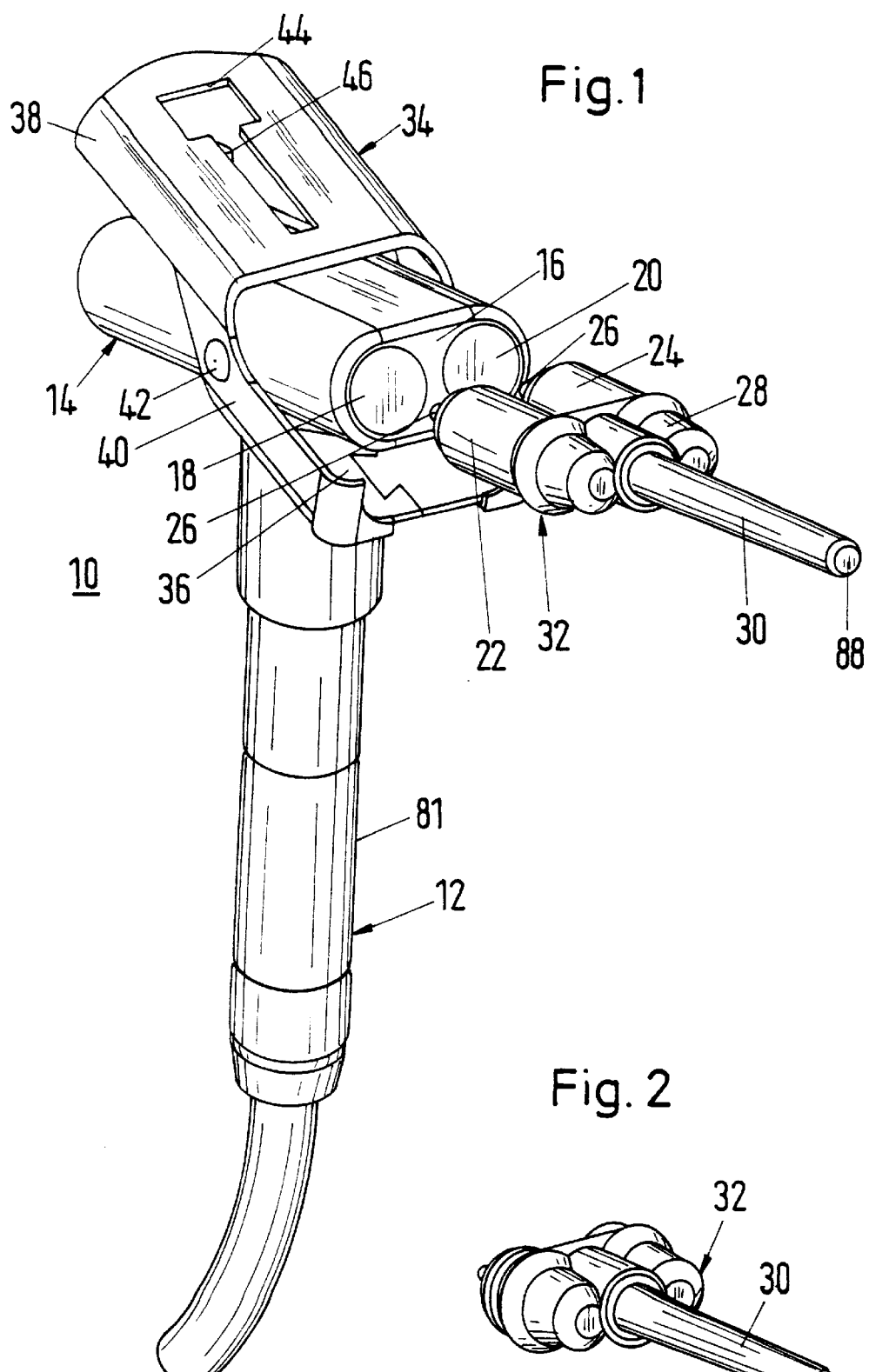
FIG. 1 is a perspective view of the manual device according to one embodiment of the invention with film bags, headpiece and static mixer not inserted in the receptacle.

A manual device 10 according to the invention is illustrated in FIG. 1. The manual device 10 is connected to an electric motor-powered rotational drive unit 12 that can be uncoupled from the manual device 10 via a first coupling 82, (see FIG. 8) which interacts with a control unit not shown here. Alternatively to this, a lamellar motor operated by compressed air can be used as a rotational drive unit.

The manual device 10 features a housing 14 that comprises a receptacle 16. The receptacle 16 consists of two mutually separated cylindrical chambers 18 and 20 which serve to accommodate film tubes 22 and 24.

A film tube 22, 24 is closed off at each of its two ends with a clip 26; see FIGS. 4–7 as well, in which the tubes can be coated with TEFLON® (tetrafluoroethylene polymer) for better sliding out of the end of the respective film tube.

The two film tubes 22 and 24 contain components of a multicomponent molding compound, such as dental impression material, and are connected to a headpiece 28. At its end the headpiece 28 features a static mixer 30, situated away from the film tubes 22, 24, which is permanently integrated into the headpiece 28 and projects in a rod shape from the latter in the direction of the film tubes 22, 24.

The outer casing 31 of the static mixer 30 is constructed to be able to rotate against the base 29. In particular, an angled nozzle 33 arranged on the static mixer 30—FIG. 2—can be oriented in this way in the appropriate treatment positions, whereby when using the manual device, for instance in conjunction with impression material in dental work, the application in the interproximal as well as in the lingual or buccal region is eased.

The film tubes 22 and 24, the headpiece 28, as well as the static mixer 30 constitute an inseparably connected constructive unit, which is removed from the manual device 10 after use and disposed of. In the following, this constructive unit is referred to as disposable unit 32.

The disposable unit 32 is inserted into the receptacle 16 such that the film tubes 22 and 24 engage the associated chambers 18 and 20 and the headpiece 28 contacts the end face of the receptacle 16.

The disposable unit 32 can be secured in the receptacle 16 by a holder 34.

The holder 34 can be pivoted about an axis which extends perpendicular to the longitudinal axis of the receptacle 16 or of the chambers 18 and 20, and has a holder part 36 arranged underneath the receptacle 16 and a holder part 38 arranged above the receptacle 16.

The lower holder part 36 extends below the receptacle 16 past the receptacle 16 in the longitudinal direction of the receptacle 16 and surrounds in places the headpiece 28 of the disposable unit 32 inserted into the receptacle 16, see FIG. 3. In this way, the disposable unit 32 is secured in the housing 14 of the manual device 10.

To the side on the holder part 36, a bar 40 is provided, which extends with the closed holder 34 parallel to the receptacle 16 up to the articulation point 42 of the holder 34 on each side of the receptacle 16 and joins together the upper holder part 38 and the lower holder part 36. The lower holder part 36 thus extends from the articulation point 42 in the direction of the disposable unit 32, whereas the upper holder part 38 extends from the articulation point 42 in the direction of the side of the housing 14 remote from the disposable unit 32.

Figure 3:
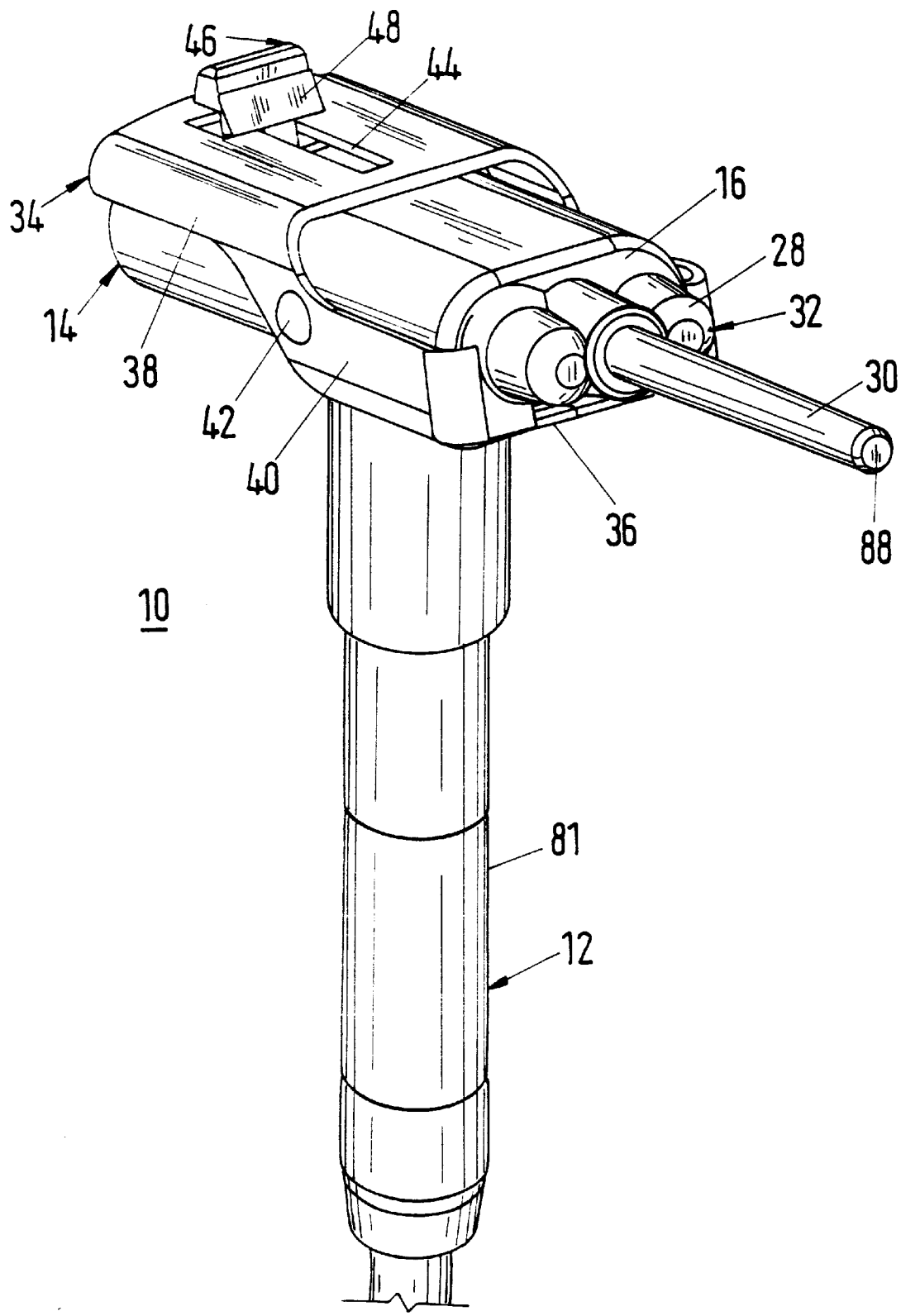
FIG. 3 is a perspective view of the manual device of FIG. 1 ready for operation.

The holder 34 can be pivoted about its articulation points 42 from a closed position holding the disposable unit 32 inside the receptacle 16, FIG. 3, into an opening position releasing the disposable unit 32, FIG. 1, and back.

In the closed position the upper holder part 38 lies on top of the upper side of the receptacle 16 and the lower holder part 36, against the lower side of the receptacle 16.

A T-shaped cutout 44 is inserted into the upper holder part 38. The T-shaped cutout 44 is associated with a second coupling 46 and a catch 48, which function in conjunction with the disposable unit 32, as will be discussed further below.

Figure 8:
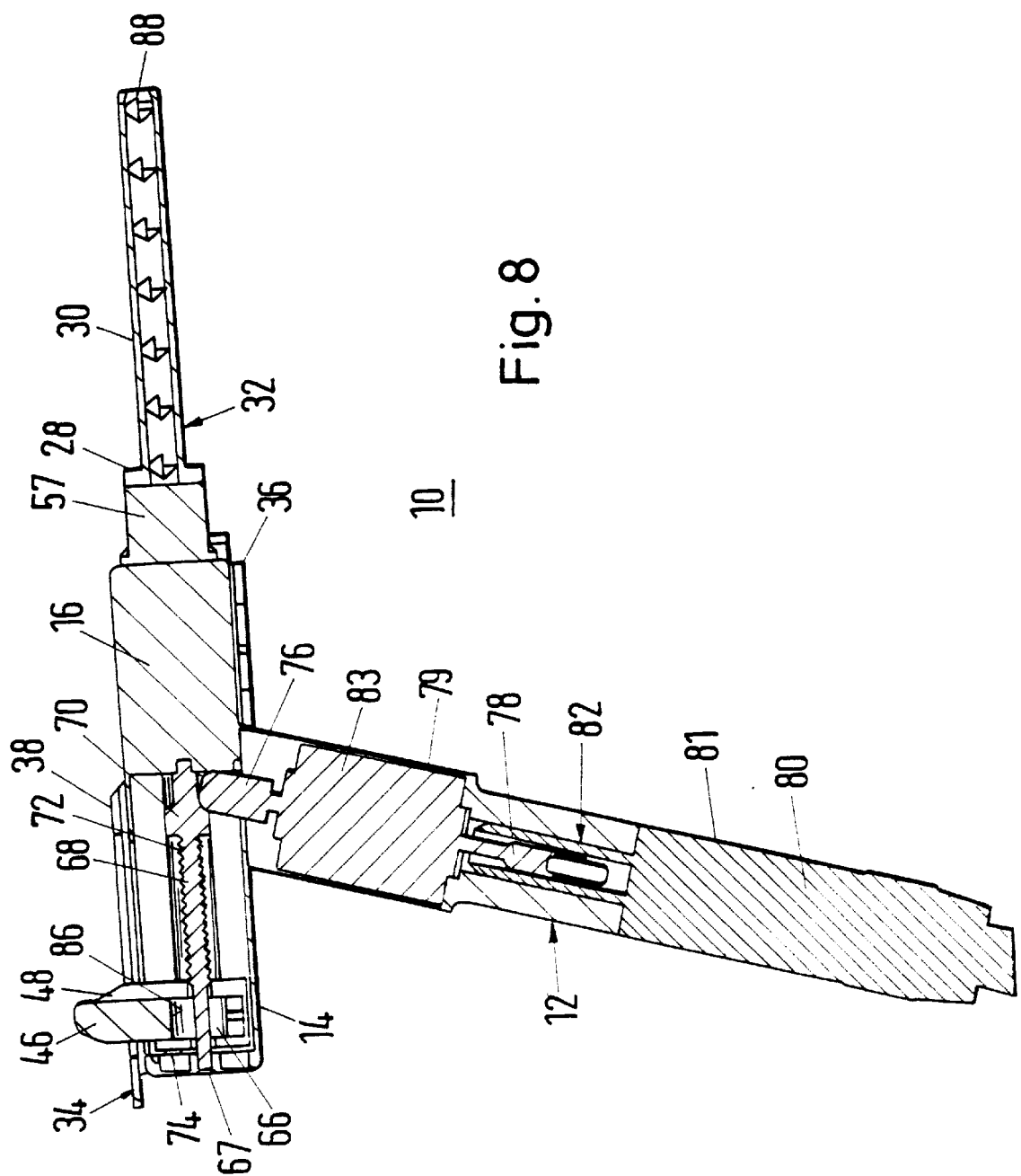
FIG. 8 is a longitudinal sectional view of the manual device.
Figure 10:
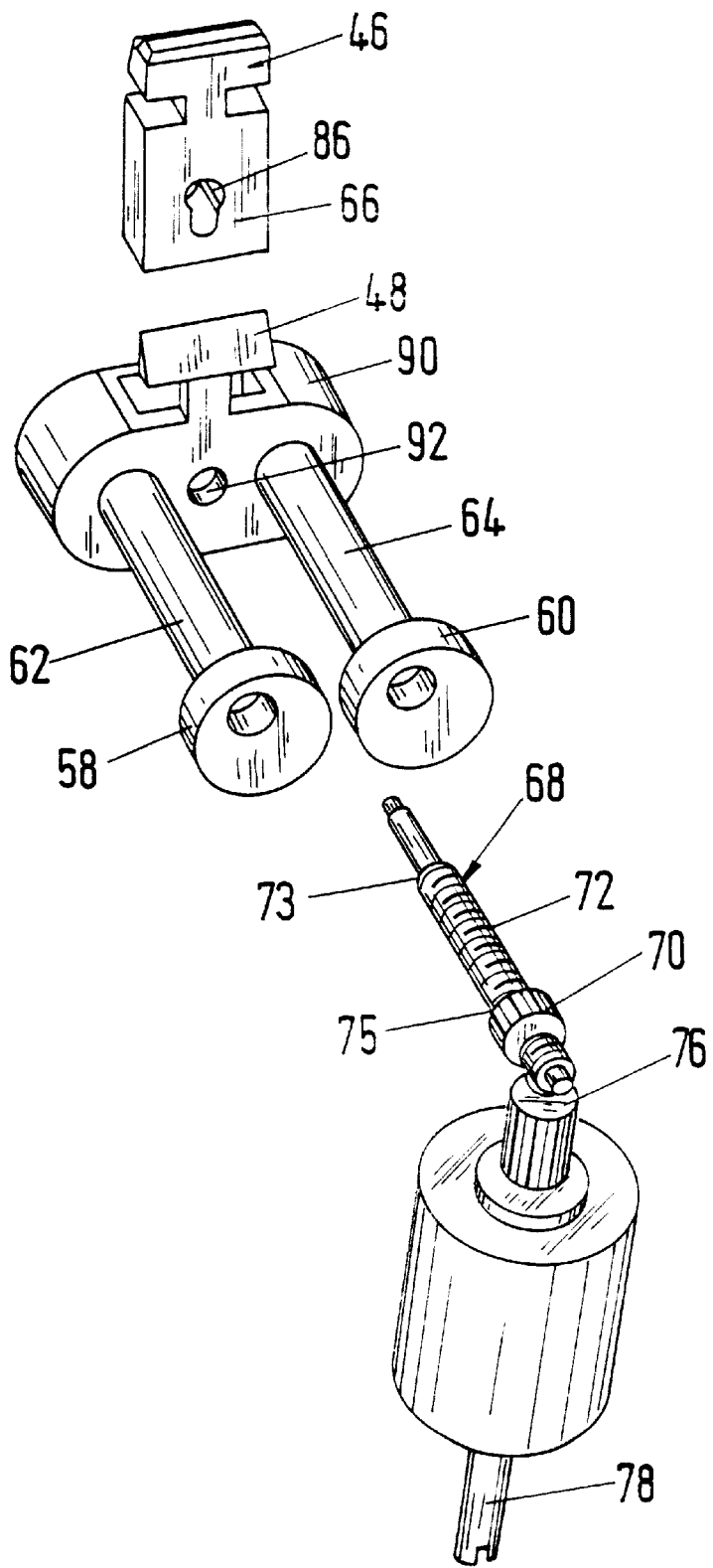
FIG. 10 is a perspective exploded view of the motive parts and pistons of the manual device of FIG. 1.

In front of the second coupling 46, a catch 48 is joined to an end piece 90—see FIGS. 8 and 10—which widens towards the bottom. With it the holder 34 is locked in its closed position. Parallel to the longitudinal axis of the receptacle 16, the end part 90, in which the second coupling 46 is inserted, is spring-loaded in the direction of the disposable unit 32—spring 74 according to FIG. 6—such that, upon closing the holder 34, the end part 90 is first moved via the catch 48 and the second coupling 46 first against the spring force by the upper holder part 36 backwards and, upon passing of the catch 48 through the cutout 44 of the holder 34, the second coupling 46 and the end part 90 with the catch 48 is again moved forward. A pivoting back of the holder 34 into the opening position is prevented by the catch 48.

After use of the manual device 10, the second coupling 46 and through it the end part 90 with the catch 48 are pressed backwards against the spring force, and the catch 48 can pass through the cutout 44 upon pivoting of the holder 34. The disposable unit 32 becomes free and can be exchanged.

Figure 2:
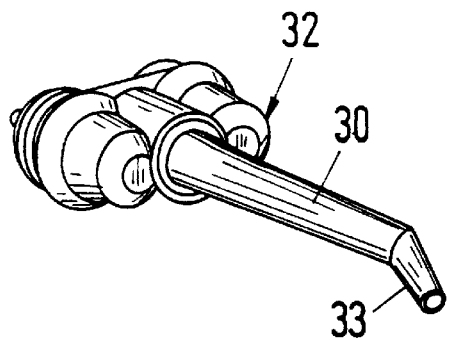
FIG. 2 is a perspective detailed view of the constructive unit consisting of headpiece, static mixer and emptied film bags, the tip being angled off.

A used disposable unit 32 is shown in perspective in FIG. 2, the static mixer 30 being equipped, as mentioned above, with an angled nozzle 33.

FIG. 4 shows the disposable unit 32 in section with filled film tubes 22 and 24. The film tubes 22,24 are closed off at their ends with the clip 26. A free end of the film tubes 22,24 engages the headpiece 28, a ring 50 of the headpiece 28 being assigned to each film tube 22,24. The ring 50 is adapted to the shape of the filled film tube 22,24 and glued, welded or the like to the associated film tube 22,24.

The headpiece 28 has flow channels 52, initially constructed in a chamber shape, connecting the associated free ends of the film tubes 22 and 24 to the static mixer 30.

For each chamber of the flow channel 52, a screen 54 is placed in front of the static mixer 30 to prevent a penetration of the chambers 26 released from the film tubes 22,24 or of parts of the film tubes 22, 24 into the static mixer 30.

The screen 54 associated with the respective chambers of the flow channel 52 is constructed in one piece with the static mixer 30. The static mixer 30 with the screen 54 is inserted into a drilled hole 56 in the headpiece 28 and glued to the headpiece 28 and thus inseparably connected to it. The screen 54 also extends over the entire cross section of the respective associated flow channel 52.

The static mixers 30 can have differing spirals, edges or the like in their passage openings, which permit a thorough mixing of the components passing through the static mixer 30 received from the film tubes 22, 24 via the flow channels 52, for instance an impression-molding compound for dental purposes. Differing configurations of a static mixer 30 are used, depending on the consistency of the components. Such static mixers 30 are known and therefore not described in further detail.

The mixing ratio of the two components is 1:1 in the present case. It can also be different, however.

The components of the two film tubes 22 and 24 are only mixed together in the static mixer 30, that is, the flow channels 52 hold the two components separated until their entry into the static mixer 30. To this end, a separation wall 57 separating the two channels 52 is provided.

In its forward area, the housing 14 of the manual device 10 has the receptacle 16 having the cylindrical chambers 18, 20. Seated in the rear area of the housing 14 are two piston rods 62, 64, at the end of which a respective piston 58, 60 is provided. A piston 58, 60 impinges into a chamber 18, 20, respectively. The pistons 58, 60 can each be moved parallel to the longitudinal axis of the receptacle 16 in the direction of the opening of the flow channel 52 pointed towards the film tubes 22 and 24 see FIG. 5.

The piston 58, 60 is connected via its piston rod 62, 64 and the end part 90 connecting the two piston rods 62, 64; see FIG. 10, to a nut 66 as part of the second coupling 46, since, as already explained, the second coupling 46 is arranged in the end part 90.

The piston 58, 60 is adapted to the shape of the free end of the filled film tubes 22,24 pointing away from the headpiece 28 and surrounds the clip 26 closing off the film tube 22,24. This prevents the clip 26 from separating from the film tube 22,24 under rising internal pressure in the film tube 22, 24.

Centered in the housing 14 between the receptacle 16 and the rear housing wall 67, a shaft 68 is seated, which features, in the area of the receptacle 16, a spur wheel 70 and, adjoining it and running away from the receptacle 16, thread 72 associated with the nut 66. The thread 72 is interrupted at the start of thread 73 and the end of thread 75, so that, upon reaching the beginning 73 or the end 75, the nut 66 is not moved any further by the shaft 68 with the thread 72. In this way damage to the manual device 10 is prevented.

The piston rod 62, 64 and the end part 90 with the catch 48 is tensioned by a spring 74 in the direction of the film tubes 22, 24. In this way, the catch 48 is held in a position that keeps the holder 34 in the closed position, as well as pressing the piston 58,60 against the associated film tube 22, 24 as soon as the disposable unit 32 is inserted into the receptacle 16 of the housing 14. Additionally, the nut 66 is pressed against the end of the thread 72.

In FIGS. 5 and 6, the position is shown in which the second coupling 46 and the end part 90 with the catch 48 is pressed backwards for opening and closing the holder 34. As soon as the holder 34 is closed, the spring 74 presses the piston rod 62,64 in the direction of the headpiece 28, and the nut 66 engages with the thread 72. As the shaft 68 rotates, the nut 66, the piston rods 62 and 64, as well as the pistons 58 and 60 are moved towards the film tubes 22 and 24, respectively.

An additional spur wheel 76 engages the spur wheel 70. The additional spur wheel 76 is joined to the rotational drive unit 12, whose angle of rotation is arranged at an angle to the angle of translation of the two pistons 58 and 60; see FIG. 8.

In FIG. 8, a longitudinal section through the manual device 10 is shown, wherein the separating wall 57 separating the flow channels 52 in front of the static mixer 30 and the wall of the receptacle 16 which separates the two cylindrical chambers 18 and 20 are visible.

The additional spur wheel 76 is connected to the rotational drive unit 12 via an ISO coupling 82 for dental hand and angle pieces. It is also possible for other couplings for hand and angle pieces to be used. For this purpose, the opposing piece 78 of the ISO coupling engages with an ISO coupling extension of the first coupling 82 for dental hand and angle pieces, which is in turn connected to a dental motor 80 of a dentistry unit. Such dental motors 80 are known in connection with hand and angle pieces with milling, drilling and grinding tools for dentistry purposes.

Via the first coupling 82 the manual device 10 can be simply and quickly detached from the dental motor 80 and the latter can be connected to a hand and angle piece for dentistry purposes.

The housing 81 of the dental motor 80, as well as the first coupling 82 and the part of the housing 14 of the manual device 10 facing downwards in regard to FIG. 8 together form a handle 79, with which the manual device 10 can be easily brought into the appropriate treatment positions for the patient. A reducing gear assembly 83, connecting the additional spur wheel 76 and the opposing piece 78 of the first coupling 82 and provided with a reduction ratio of 250 or 1000 to 1, is inserted into the handle 79.

Figure 9:
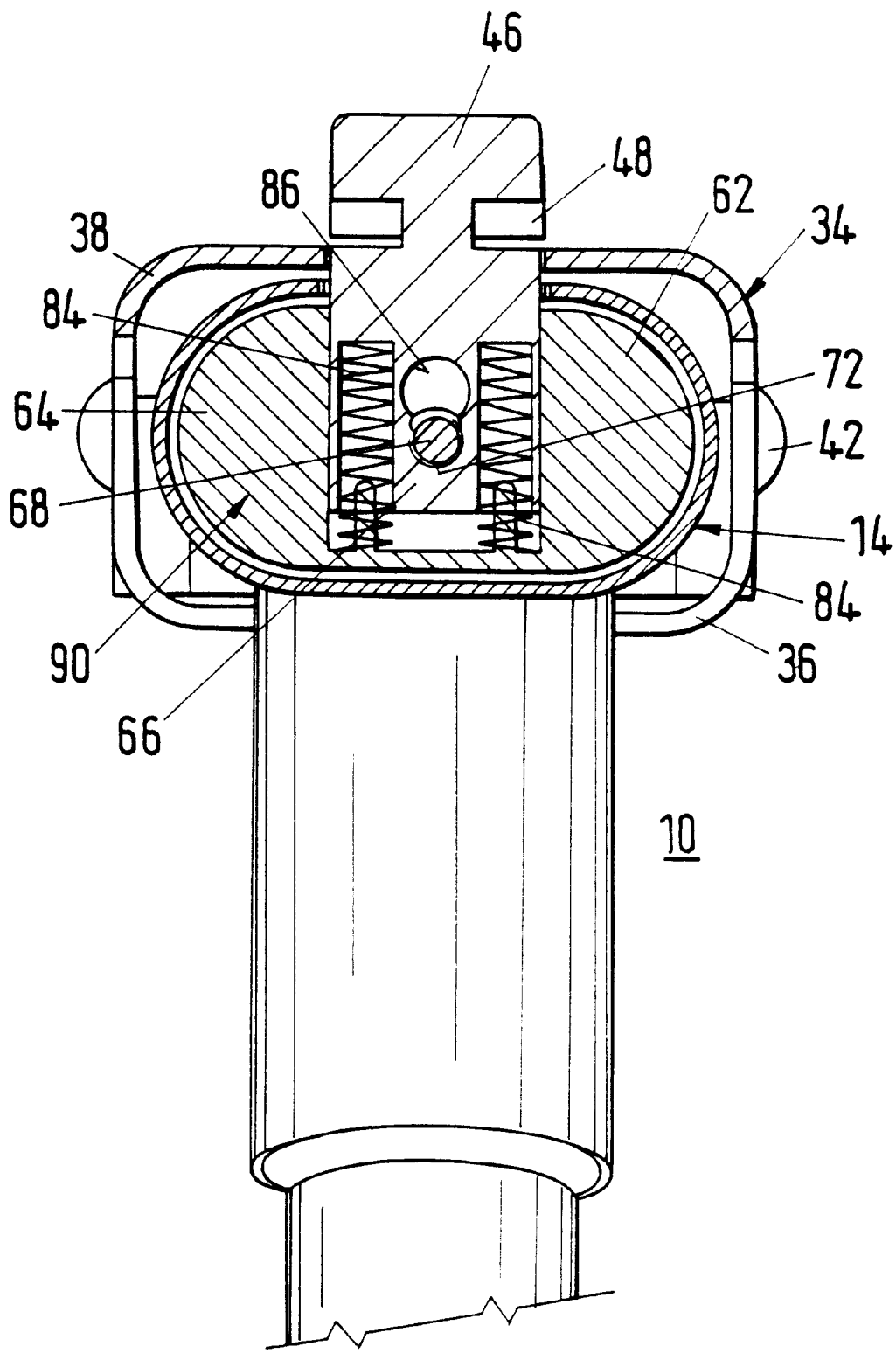
FIG. 9 is a rear view of the manual device with a partial section.

In FIG. 9, a rear view of the manual device 10 with a partial section is shown, wherein the construction of the second coupling 46 is clarified in this illustration. The second coupling 46 is solidly seated in the end part 90 connecting the piston rods 62 and 64 and is movable in the vertical direction against the force of two springs 84.

In the lower area of the second coupling 46, the nut 66, which surrounds the shaft 68 in part, is provided. The springs 84 press the nut 66 against the shaft 68. Adjoining the nut 66, open towards the top, on the side opposite from the springs 84 is a cutout 86 which is made larger than the shaft 68.

In the position shown in FIG. 9, the nut 66 engages with the thread 72 of the shaft 68. As the drive motor 80 turns, the reduction gear assembly 83 and the spur wheel 76 are moved via the first coupling 82 and in turn drive the spur wheel 70 and thus the shaft 68. As the shaft 68 turns, the nut 66, together with the second coupling 46, the attached end part 90, the piston rods 62 and 64 and the pistons 58 and 60 attached to them are moved in the direction of the respective opening of the flow channels 52 facing the film tubes 22 and 24.

In parallel with this, the internal pressure in the film tubes 22 and 24 rises so strongly that the respective clips 26 detach from the film tubes 22 and 24 and the individual components in the film tubes 22 and 24 are pressed via the flow channels 52 into the static mixer 30 and are mixed there. The mixed substance, in the present case a two-component molding compound, for instance, an impression-molding compound for dentistry purposes, is discharged via the output nozzle 88.

Alternatively, the films of the film tubes 22,24 can be formed weakened in the end area, by laser material removal, for instance. The removal extends, for instance, in linear form nearly over the circumference, but not entirely. This has the effect that the broken end of the film tube 22,24 remains connected to the film tube 22,24. The screen 54 is therefore not closed off, and the output of components from the film tubes 22,24 into the static mixer 30 is not hindered.

After use, the disposable unit 32 is removed in the prescribed manner from the manual device 10, and a new one with full film tubes 22 and 24 is inserted.

In order that the pistons 58 and 60 again have the complete stroke motion available for a newly inserted disposable unit 32, the second coupling 46 is pressed downwards against the springs 84. The shaft 68 is thereby arranged in the opening 86 of the nut 66. The second coupling 46 with the piston rods 62 and 64, as well as the pistons 58,60, can now be displaced against the force of the spring 74 in the direction of the rear housing wall 67. If the second coupling 46 is released, the nut 66 again engages with the thread 72 because of the force of springs 74 and 84 and can again move the pistons 58 and 60 against the film tubes 22,24 as the shaft 68 turns.

In FIG. 10, the moving parts are again shown individually in perspective exploded view. Here it becomes clear that the piston rods 62 and 64 engage the shared end part 90, in which the second coupling 46 is seated, and that the end part 90 has the catch 48.

It ought to be clear that the drilled hole 92 illustrated in the end part 90 is larger than the shaft 68.

An alternative drive unit is shown in FIGS. 11 and 12, the manual device 10 being constructed otherwise in the manner already described. The drive unit 94 comprises a battery-driven motor seated in a motor housing 96, and likewise comprising a first coupling for hand and angle pieces 104. The motor housing 96 is constructed so as to accommodate batteries or storage batteries. The motor is controlled via a switch 98.

Figure 13:
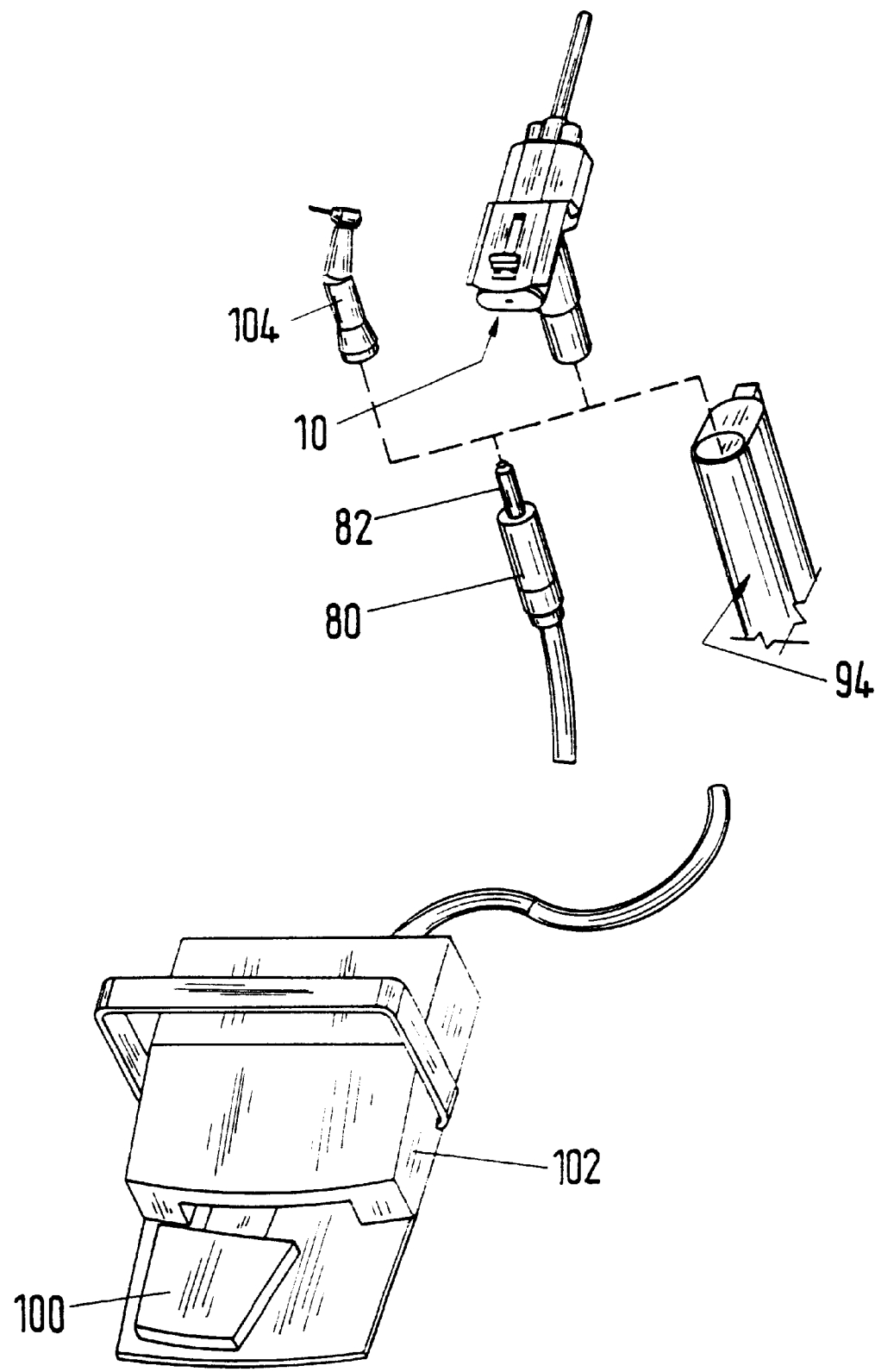
FIG. 13 is a perspective view of the various combination possibilities of the manual device.

The flexible design of the manual device 10 according to the invention becomes clear from FIG. 13. The dental motor 80 of a dentistry unit is connected to a control unit 102 featuring a foot pedal 100, with which the motor 80 is controlled. An angle piece 104 or the manual device 10 according to the invention can be connected to the first coupling 82 on the output side of the motor 80.

Thus impression-molding compounds that consist of two or more curable components can be applied by the dentist easily and in a sterile fashion with the manual device 10.

An additional advantage should also be seen in the fact that the dentist can control the amount of molding compound that can be delivered by way of the motor speed with the foot pedal 100, without the dentist's hand being needed or any force expended. The dentist can concentrate entirely and completely on applying the molding compound to the part of the patient to be treated. Moreover, a dental motor 80 already available in the practice is better utilized.

If a dental motor 80 is not available, recourse can be made to the battery-operated drive unit 94.

List of Reference Numbers

10 Manual device
12 Rotational drive unit
14 Housing
16 Receptacle
18 Chamber, left
20 Chamber, right
22 Film tube, left
24 Film tube, right
26 Clip
28 Headpiece
29 Base
30 Static mixer
31 Outer shell
32 Disposable unit
33 Nozzle
34 Holder
36 Holder part, lower
38 Holder part, upper
40 Bar
42 Articulation point
44 Cutout
46 Second coupling
48 Catch
50 Ring
52 Flow channel
54 Screen
56 Drilled hole
57 Separating wall
58 Piston 60 Piston
62 Piston rod
64 Piston rod
66 Nut
67 Rear housing wall
68 Shaft/output shaft
70 Spur wheel
72 Thread
73 Start of thread
74 Spring
75 End of thread
76 Additional spur wheel
78 Opposing coupling piece
80 Dental motor
81 Motor housing
82 First coupling
83 Reduction gear assembly
84 Spring
86 Cutout
88 Delivery nozzle
90 End part
92 Drilled hole
94 Drive unit
96 Motor housing
98 Switch
100 Pedal
102 Control unit
104 Angle piece The invention is distinguished by its simple design and broad application possibilities While preferred embodiments of the invention have been shown and described, it will be understood by one skilled in the art could make various changes on modifications without varying from the scope of the invention.

I claim:

1. A dental handpiece for mixing and delivering a multi-component molding compound consisting of a mix of individual components for dentistry purposes, the device comprising a receptacle (16), pistons (58, 60) located adjacent the receptacle for movement therein, the pistons operated by a drive unit, at least two film bags (22, 24) each filled with an individual component of the multicomponent molding compound, each film bag having closed off ends which open under rising internal pressure produced via the pistons (58, 60), a static mixer (30) into which the individual components can be transferred from the film bags (22,24), and a headpiece (28) that is inseparably connected to the film bags (22, 24) having accommodation surfaces (50) on its side facing the film bags (22, 24) arranged symmetrically to an entry opening of the static mixer (30) and adapted to the shape of the film bags (22, 24), to which the film bags (22, 24) are permanently joined, and having at least two separated flow channels (52) open towards the film bags (22,24) and communicating with the static mixer (30), the static mixer (30), the headpiece (28) and the film bags (22, 24) formed as an inseparably connected constructed unit (32) which is disposable, the unit inserted into and removed from the receptacle (16) of the device (10).

2. A dental handpiece according to claim 1, further comprising means for screening (54), inserted between the flow channels (52) and the static mixer (30).

3. A dental handpiece according to claim 2, wherein each flow channel (52) extends essentially vertical to a longitudinal axis of the film bags (22, 24) up to the means for screening (54) and, following the means for screening, extends essentially in the longitudinal direction of the static mixer (30).

4. A dental handpiece according to claim 2, wherein at least part of the static mixer (30) is constructed in one piece with the means for screening (54).

5. A dental handpiece according to claim 4, wherein each flow channel (52) extends essentially vertical to a longitudinal axis of the film bags (22, 24) up to the means for screening (54) and, following the means for screening, extends essentially in the longitudinal direction of the static mixer (30).

6. A dental handpiece according to claim 1 wherein at least an end of each film bag (22, 24) turned towards the headpiece (28) is closed off with a clamping element (26), which detaches from the film bag (22, 24) under increasing internal pressure, to form a delivery opening in the film bag (22, 24).

7. A dental handpiece according to claim 1,wherein an end of each film bag (22, 24) turned towards the headpiece (28) has a material weakening in the film of the film bag (22, 24), which serves as a planned rupture point that opens under increasing internal pressure in the film bag (22, 24).

8. A dental handpiece according to claim 1, wherein the static mixer (30) has an outer shell (31) and a base (29) and the outer shell (31) is seated so as to rotate with respect to the base (29).

9. A dental handpiece according to claim 1, wherein the static mixer (30) has an angled-off nozzle (33).

* * * * *